US005602184A

United States Patent [19]

[11] Patent Number: 5,602,184

Myers et al.

[45] Date of Patent: Feb. 11, 1997

[54] MONOTERPENES, SESQUITERPENES AND DITERPENES AS CANCER THERAPY

[75] Inventors: Charles E. Myers, Rockville; Jane Trepel, Bethesda; Edward Sausville, Silver Spring; Dvorit Samid, Rockville; Alexandra Miller, Hyattsville; Gregory Curt, Rockville, all of Md.

[73] Assignee: The United States of America as represented by Department of Health and Human Services, Washington, D.C.

[21] Appl. No.: 25,471

[22] Filed: Mar. 3, 1993

[51] Int. Cl.[6] .......... H61K 31/045

[52] U.S. Cl. .......... 514/739

[58] Field of Search .......... 514/739

[56] References Cited

U.S. PATENT DOCUMENTS 5,243,094 9/1993 Borg .......... 568/822

FOREIGN PATENT DOCUMENTS 0285302 10/1988 European Pat. Off. .
0393973 10/1990 European Pat. Off. .
2270544 11/1987 Japan .
3098562 4/1991 Japan .
9218465 10/1992 WIPO .

OTHER PUBLICATIONS

Crowell, P. L., et al., "Human metabolism of orally administered d–limonene," *Proc. Amer. Assoc. Cancer Res.*, vol. 33, p. 524, No. 3134 (Mar. 1992).

Crowell, P. L., et al., "Selective Inhibition of Isoprenylation of 21–26–kDa Proteins by the Anticarcinogen d–Limonene and Its Metabolites," *J. Biol. Chem.* 266(26):17679–17685 (Sep. 15, 1991).

Elegbede, J. A., et al., "Regression of Rat Primary Mammary Tumors Following Dietary d–Limonene," *JNCI* 76(2):323–325 (Feb. 1986).

Wattenberg. L. W., et al., "Inhibition of 4–(methylnitrosamino)–1–(3–pyridyl)–1–butanone carcinogenesis in mice by D–limonene and citrus fruit oils," *Carcinogenesis* 12(1):115–117 (1991).

"d–Limonene, an Anticarcinogenic Terpene," *Nutrition Reviews* 46(10):363–365 (Oct. 1988).

Elson, C. E., et al., "Anti–carcinogenic activity of d–limonene during the initiation and promotion/progression stages of DMBA–induced rat mammary carcinogenesis," *Carcinogenesis* 9(2):331–332 (1988).

Webb, D. R., et al., "Assessment of the Subchronic Oral Toxicity of d–Limonene in Dogs," *Fd Chem. Toxic* 28(10):669–675 (1990).

Maltzman, T. R. et al., "The prevention of nitrosomethylurea–induced mammary tumors by d–limonene and orange oil," *Carcinogenesis* 10(4):781–783 (19890.

Carter, B. S., et al., "*ras* Gene Mutations in Human Prostate Cancer," *Cancer Research* 50:6830–3832 (Nov. 1, 1990).

Isaacs, W. B., et al., "Genetic Changes Associated with Prostate Cancer in Humans," *Cancer Surveys* vol. 11 (Prostate Cancer), 15–24 (1991).

Casey, P. J., et al., "p21ras is modified by a farnesyl isoprenoid," *Proc. Natl. Acad. Sci. USA* 86:8323–8327 (Nov., 1989).

*Primary Examiner*—Jerome D. Goldberg
*Attorney, Agent, or Firm*—Townsend and Townsend and Crew LLP

[57] ABSTRACT

The invention provides methods of treating cancer including administering an effective amount of selected terpenes to a mammal having the cancer when the cancer is prostate cancer, colon cancer, astrocytoma, or sarcoma. The terpene is selected from the group consisting of a cyclic monoterpene, a noncyclic monoterpene, a noncyclic sesquiterpene and a noncyclic diterpene. The invention also provides a method of sensitizing a cancer to radiation including administering an effective amount of a terpene to a mammal having the cancer wherein the terpene is selected from the group noted above. Additionally, the invention provides methods of inhibiting the growth of cancer cells including applying an effective amount of a selected terpene to the cancer cells which are cells of prostate cancer, colon cancer, osteosarcoma, or glioblastoma.

19 Claims, 13 Drawing Sheets

MONOTERPENES, SESQUITERPENES AND DITERPENES AS CANCER THERAPY

BACKGROUND OF THE INVENTION

Treatment of human cancer is an area of clinical medicine which remains fraught with complications and which often presents an array of suboptimal treatment choices. For example, prostate cancer, which is the most common cancer in men and the second leading cause of cancer death in men, can be treated surgically or medically or with a combination of both depending on the state of advance of the cancer. Other than hormonal therapy, no agents are available to treat prostate cancer that are without substantial toxicity. Frequently, cancer occurs in debilitated patients who are either not surgical candidates or who could not tolerate conventionally available chemotherapeutic agents.

Radiation therapy (X-ray treatment) is one modality available to treat selected cancers. It is used at many stages in the treatment of prostate cancer. For example, it can be used as an alternative to surgery to treat localized prostate cancer. X-ray therapy can also be used in metastatic prostate cancer to treat local deposits of tumor that threaten key organs such as the spinal cord. Radiation can be useful to treat a number of cancers in settings such as to attempt the cure of local tumor and the symptomatic management of troublesome metastatic disease.

Osteosarcoma is an example of a cancer primary to the bone but which can metastasize and which remains a major tumor problem in children. A subtype of osteosarcoma, chondrosarcoma, does not metastasize. However, chondrosarcoma often recurs locally after surgical excision and it can require more than surgery alone. Glioblastomas are malignant tumors which do not metastasize generally but which are commonly beyond surgical cure, with median patient survivals of less than one year. A rapidly growing primary tumor that is not surgically curable can cause significant morbidity and mortality without necessarily metastasizing. In such a case, effective chemotherapy is needed.

More generally, a chemotherapeutic agent which possesses little or no toxicity, which is inexpensive to obtain or manufacture, which is well tolerated by the patient, and which is easily administered would be a desirable addition to the array of therapeutic modalities available to the oncologist. Such a chemotherapeutic agent could find application in treatment of cancers which are metastatic, locally expanding or locally invasive. Additionally, such an agent could be useful if it were to sensitize the cancer to radiation therapy. Thus, the cancer would respond more readily to X-ray treatment.

SUMMARY OF THE INVENTION

The invention provides methods for treating certain cancers comprising administering an effective amount of selected terpenes to a mammal having a cancer susceptible to such treatment. Most preferably, the cancer is an adenocarcinoma of the prostate or colon, a glioblastoma or a sarcoma such as an osteosarcoma. Preferably the administration is accomplished by the oral route and is given one to three times a day. The terpenes are acyclic monoterpenes such as beta-myrcene or citral, cyclic monoterpenes such as limonene, acyclic sesquiterpenes such as farnesol or nerolidol, or acyclic diterpenes such as phytol or geranylgeraniol. Preferably, the mammal treated is a human although the invention can have other applications such as veterinary use.

Additionally, the invention provides a method of sensitizing a cancer to subsequent radiation treatment. This method includes administering an effective amount of a terpene to a mammal having the cancer. The most preferred cancers, terpenes, and administration are as stated above.

The invention also includes a method of inhibiting cancer cell growth comprising applying an effective amount of a terpene to the cancer cells. The most preferred cancers and terpenes are as stated above. If the cells are located in a mammal, the application is preferably either oral or topical and one to three times a day.

Figure 1:
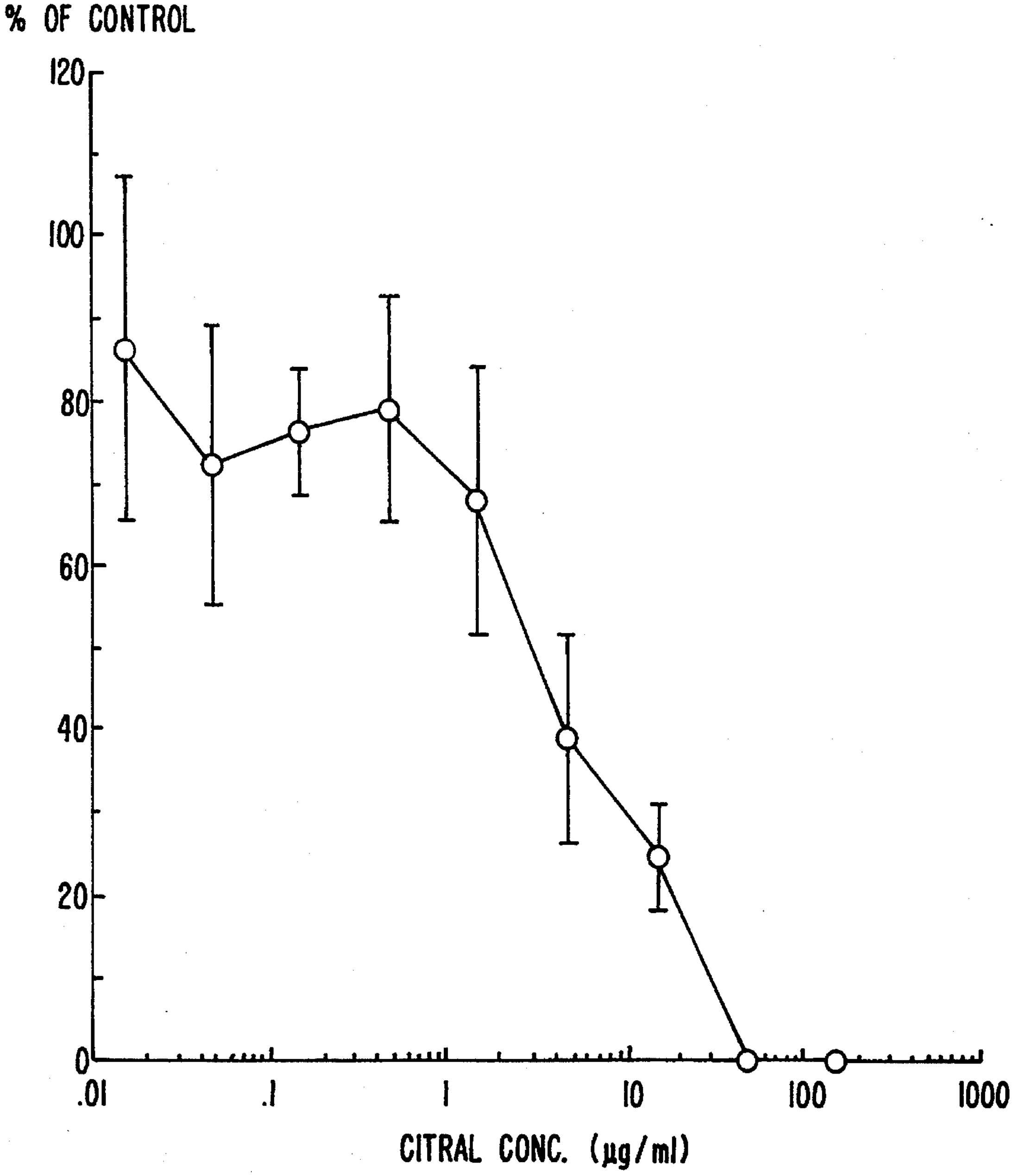
FIG. 1 graphs the growth of prostate cancer cells as a percentage of untreated control cells against the concentration of citral in micrograms per milliliter (μg/ml) added to the growth medium.
Figure 2:
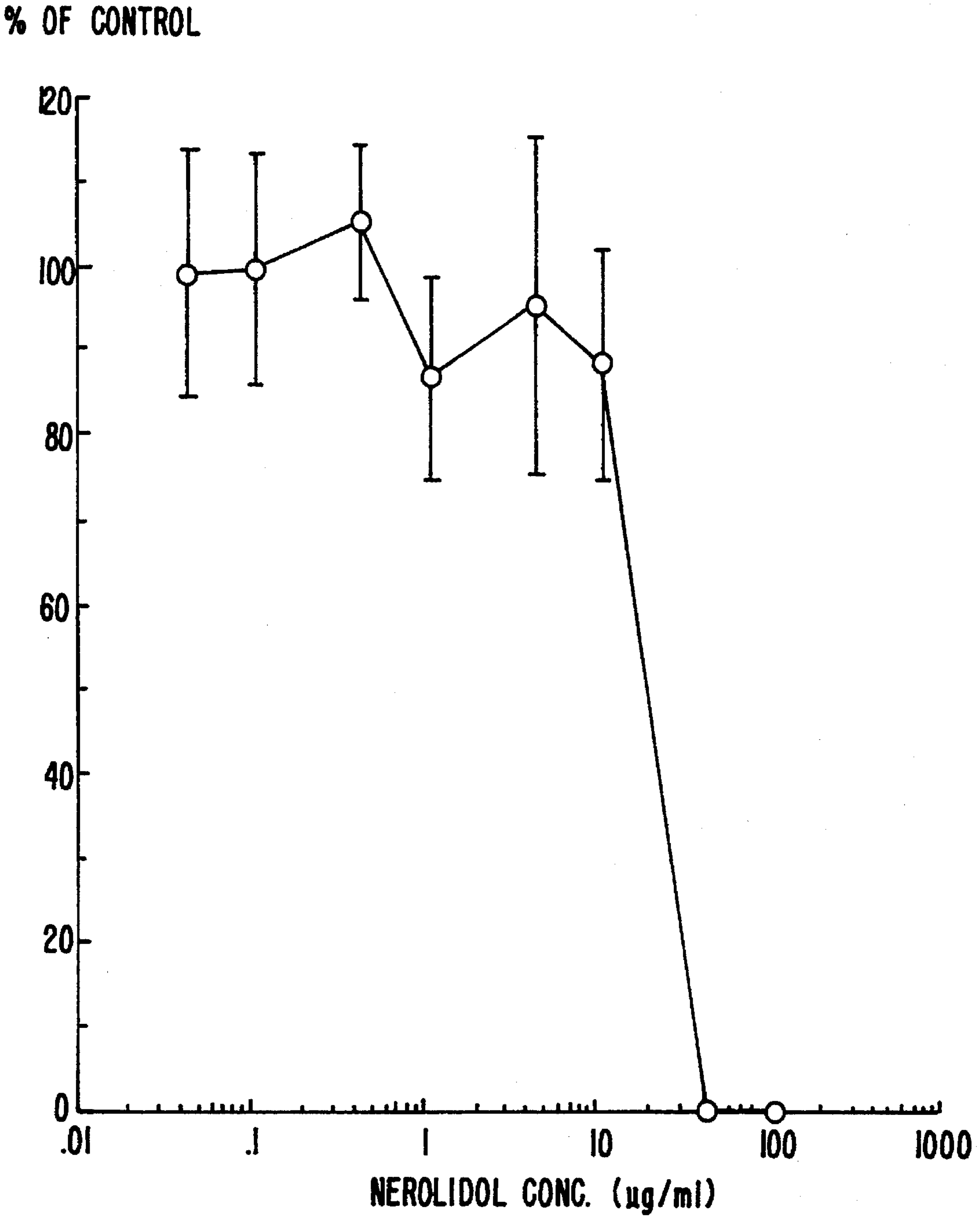
FIG. 2 graphs the growth of prostate cancer cells as a percentage of untreated control cells against the concentration of nerolidol in μg/ml added to the growth medium.
Figure 3:
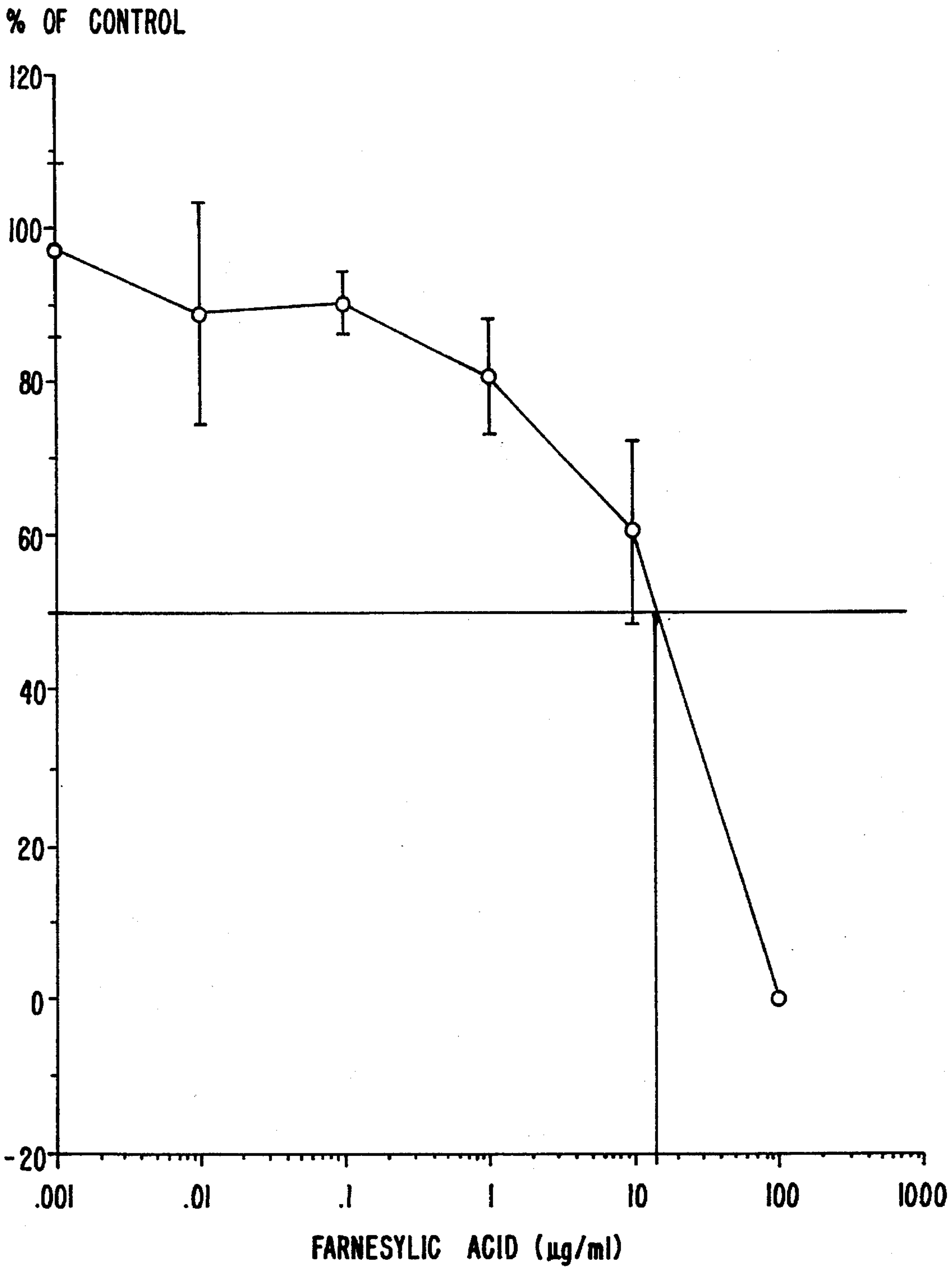
FIG. 3 graphs the growth of prostate cancer cells as a percentage of untreated control cells against the concentration of farnesylic acid in μg/ml added to the growth medium.
Figure 4:
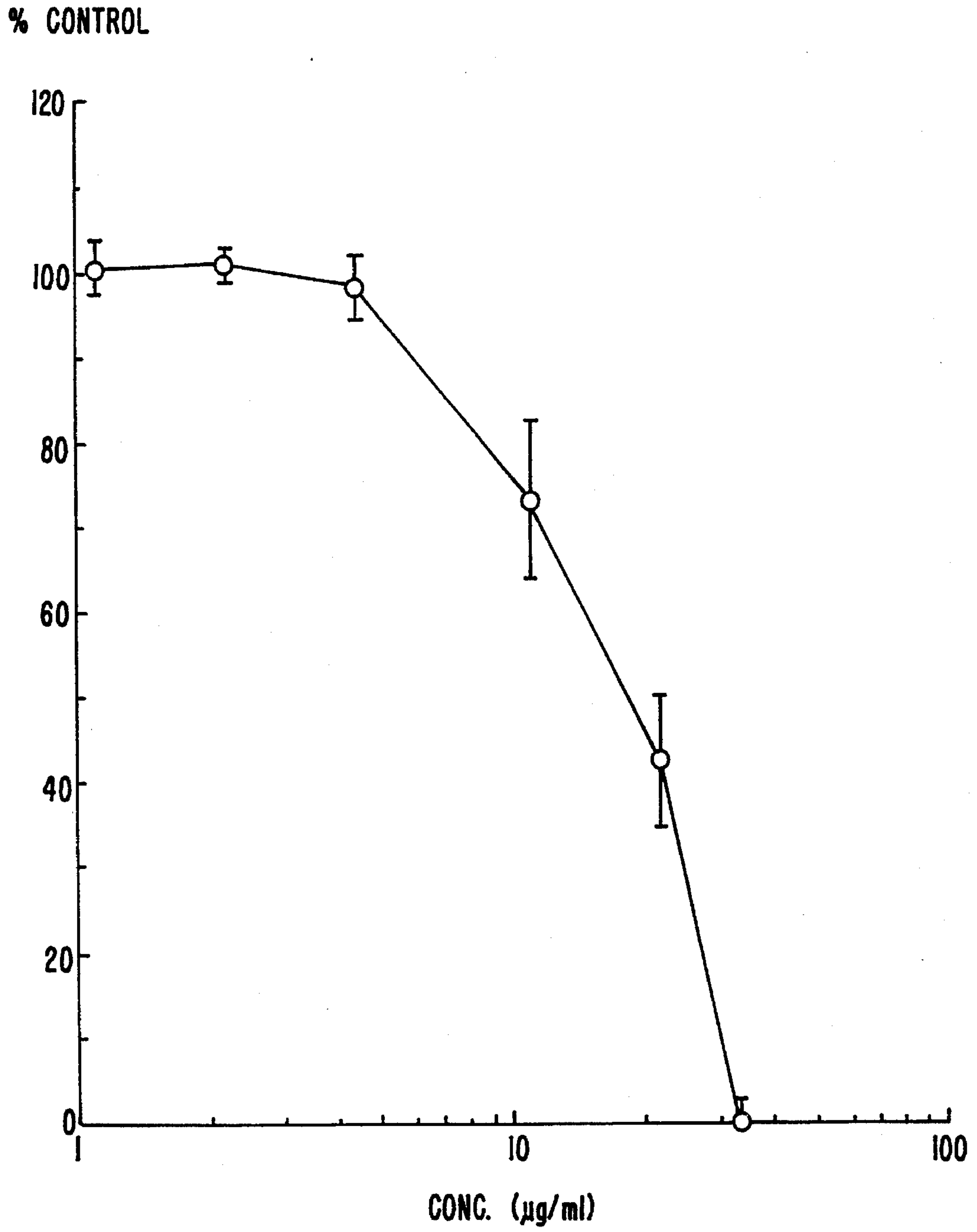
FIG. 4 graphs the growth of prostate cancer cells as a percentage of untreated control cells against the concentration of farnesol in μg/ml added to the growth medium.
Figure 5:
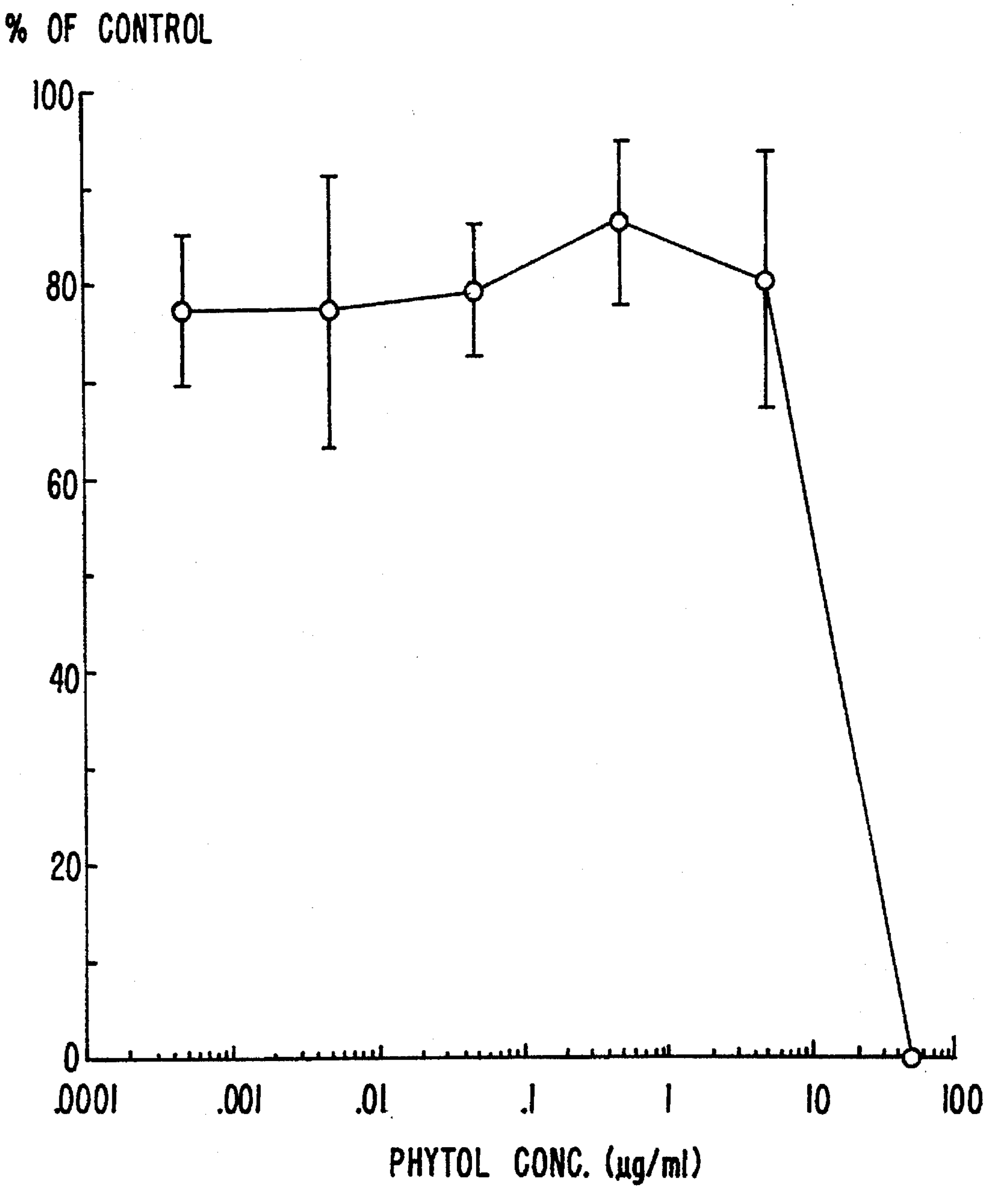
FIG. 5 graphs the growth of prostate cancer cells as a percentage of untreated control cells against the concentration of phytol in μg/ml added to the growth medium.
Figure 6:
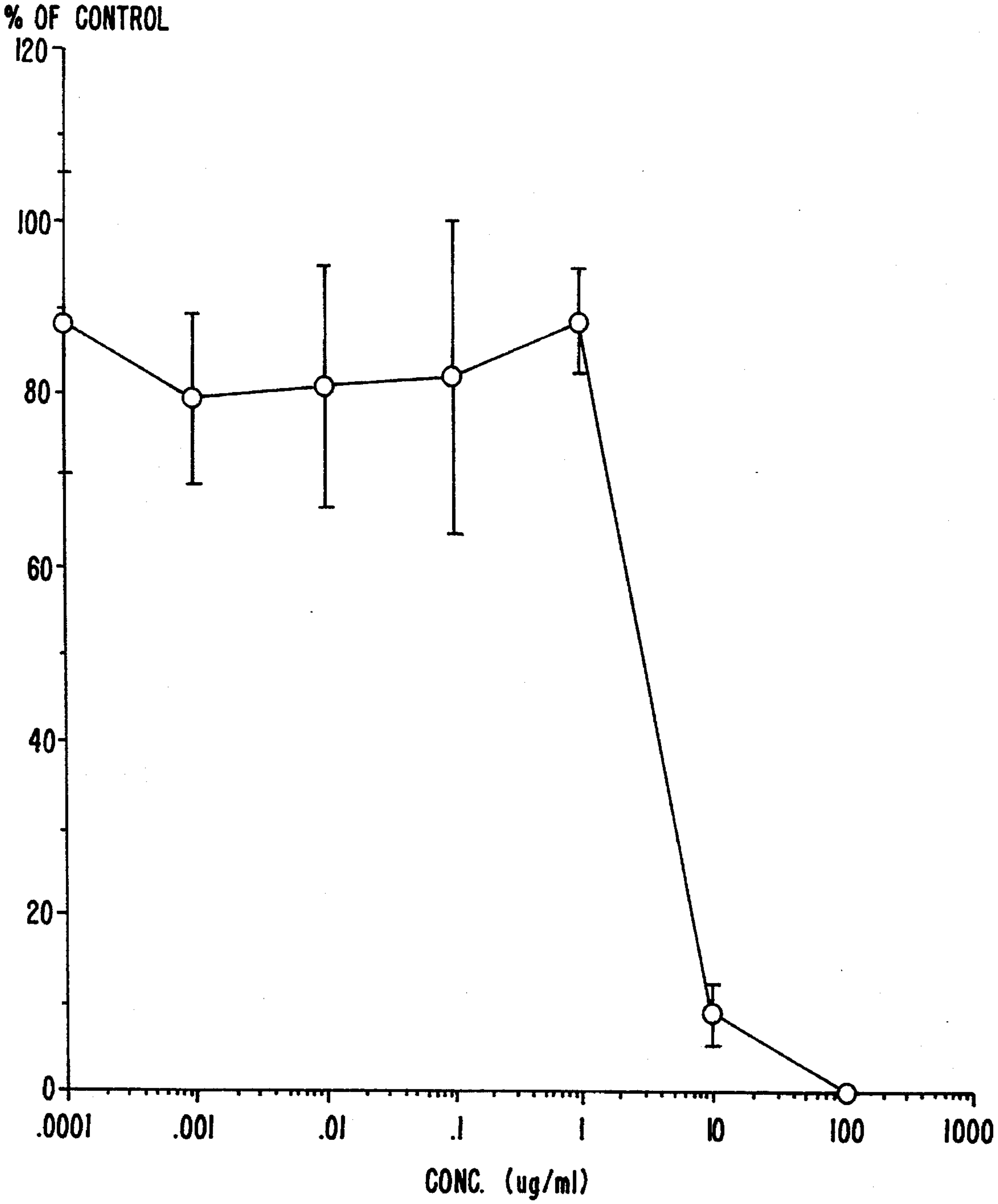
FIG. 6 graphs the growth of prostate cancer cells as a percentage of untreated control cells against the concentration of geranylgeraniol in μg/ml added to the growth medium.

The tumor volume in $mm^3$ is plotted against the terpene dose in gm/kg/day.

DETAILED DESCRIPTION OF THE PREFERRED EMBODIMENT

The invention includes methods of treating selected cancers comprising administering an effective amount of a terpene to a mammal having the cancer. The cancer is selected from a group consisting of prostate cancer, colon cancer, astrocytoma and sarcoma. The terpene is selected from the group consisting of a cyclic monoterpene, a noncyclic monoterpene, a noncyclic sesquiterpene and a noncyclic diterpene.

Terpenes of the Invention

Terpenes are organic compounds constructed of multiples of the 5-carbon hydrocarbon isoprene unit or 2-methyl-1,3 butadiene ($CH_2$:CMe.CH:$CH_2$). Terpenes containing two isoprene units are called monoterpenes, those containing three such units are sesquiterpenes, and those having four isoprene units are diterpenes. Additionally, higher order terpenes exist and there is no set upper limit to how many isoprene units a terpene may include. For example, natural rubber is a terpene with approximately 60 isoprene units. For information about the structure and synthesis of terpenes, including terpenes of the invention, see Kirk-Othmer Encyclopedia of Chemical Technology, Mark, et al., eds., 22:709–762 3d Ed (1983).

The term cyclic means that the compound includes a ring structure such as a six carbon ring. The term noncyclic means that the compound does not include a ring structure but rather is linear in its formulaic depiction. In general, a double bond between the α and β carbons relative to the —OH must be present if an —OH is present. An α carbon is the carbon adjacent to the carbon which bears the functional group. That is, the α carbon is not the carbon attached to the hydroxyl (—OH) group. For example, if the compound is an alcohol, the α carbon is not the carbon to which the —OH group is attached but rather the adjacent carbon. The β carbon is the carbon adjacent to the α carbon moving in the opposite direction from the hydroxyl group. If the functional group is a carboxylic acid group (—COOH), then the α carbon is not the carbon included in the COOH group but rather the adjacent carbon. The β carbon is the carbon adjacent to the α carbon moving in the direction away from or opposite to the functional group which in this example is a COOH group.

The general formula for a cylic monoterpene is displayed in formula 1. $R^1$ and $R^2$ are independently selected from the group including the lower alkyls, the lower alkenes, a hydroxyl, a carboxyl, a carboxylic acid group, and a hydrogen atom. The ring structure preferably includes a double bond, the placement of which depends on the precise location of the $R^1$ and $R^2$ groups. The term lower alkyl or power alkenes refers to structures containing no more than four carbons.

The acylic monoterpenes are represented generally by formula 3. $R^1$, $R^2$ $R^3$ and $R_4$ are independently selected from the group including the lower alkyls, lower alkenes, a hydroxyl group, a hydrogen atom and a carboxyl or carboxylic acid group. The acyclic monoterpene preferably includes two or more double bonds. The placement of the double bonds varies with the substitution of the R groups.

The sesquiterpenes are generally represented by formula 6. $R^1$, $R^2$, $R^3$, $R^4$, $R^5$ and $R^6$ are independently selected from the group consisting of lower alkyls, lower alkenes, hydrogen, hydroxyls, carboxylic acid and hydroxy groups. The structure preferably includes three double bonds, the placement of which varies with the substitutions selected.

The diterpenes are represented generally by formula 9. $R^1$, $R^2$, $R^3$, $R^4$, $R^5$ and $R^6$ are independently selected from the group including the lower alkyls, lower alkenes, hydrogen hydroxy, hydroxyl oxygen, carboxylic acid groups. The structure preferably includes one or more double bonds, the placement of which may vary.

Preferred Terpenes of the Invention

Drugs useful in the invention have two, three or four isoprene units. Larger structures are insoluble in aqueous solutions and may be solids at room temperature. In the invention, activity of the terpenes increases proceeding from monoterpenes to sesquiterpenes to diterpenes. Examples in increasing order of activity include limonene, farnesol, phytol and geranylgeranol.

The more active compounds, such as farnesol, phytol and geranylgeranol, all have terminal hydroxy (—OH) groups. Limonene is rapidly metabolized in vivo to compounds having terminal hydroxy groups. Also, in vivo, these alcohols undergo rapid metabolism to the corresponding aldehydes and carboxylic acids. Such corresponding structures, that is the aldehyde or carboxylic acid, can add to the activity of the parent compound. For instance, farnesylic acid is an active compound which is identical to farnesol, an alcohol, except that the former terminates in a carboxylic acid group. Citral, a monoterpene having a terminal aldehyde, is also active.

Limonene (formula 2) is an example of a cyclic monoterpene. Examples of acyclic monoterpenes are beta myrcene (formula 4) and citral (formula 5). Examples of sesquiterpenes include farnesol (formula 7), farnesal (the aldehyde of farnesol), farnesylic acid (the carboxylic acid of farnesol) and nerolidol (formula 8). Examples of diterpenes are phytol (formula 11) and geranylgeraniol (formula 10). Limonene and citral are available from Sigma Chemical Company (P.O. Box 14508, St. Louis, Mo. 63178-9916). Farnesol and phytol are available from Aldrich (1001 W. St. Paul Ave., Milwaukee, Wis. 53233). Gerarylgeraniol is available from American Radiolabeled Chemicals, Inc. The artisan will be aware of modifications which would not significantly reduce the terpene's usefulness. For example, the placement of hydroxy groups or modification to alcohols, aldehydes, and carboxylic acids are noted above. See generally Kirth-Othmer, cited above.

Formula No.:

1. Cyclic Monoterpenes

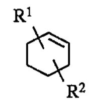

2. d-Limonene

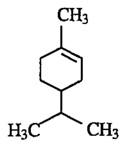

3. Acyclic Monoterpenes

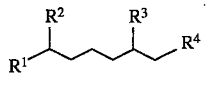

-continued

4. Beta myrcene

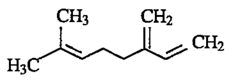

5. Citral

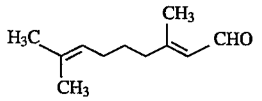

6. Sesquiterpenes

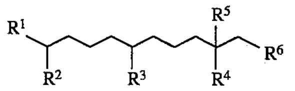

7. Trans, trans farnesol ("t,t farnesol")

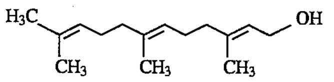

8. Nerolidol

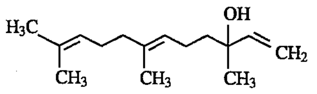

9. Diterpenes

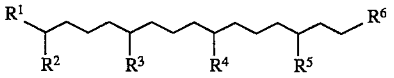

10. Geranylgeraniol

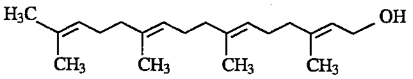

11. Phytol

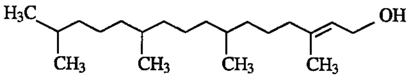

Analogs, Homologs and Derivatives

The preferred compounds are farnesol, geranylgeranol and the gernanylgeranol analog, phytol. These compounds are oxidized enzymatically to the corresponding aldehyde and carboxylic acids. These carbonyl metabolites are alpha, beta-unsaturated compounds and as such have the capacity to participate in a range of nucleophilic and electrophilic addition reactions.

Nucleophilic and Electrophilic Addition and Alpha, Beta Unsaturated Carbonyls:

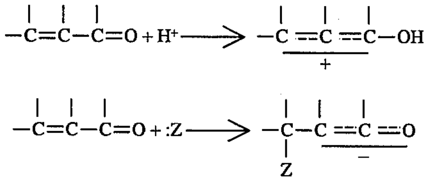

Note that a similar reaction occurs with carboxylic acids, which also contain carbonyls. Z may be any naturally occurring amino acid able to act as a nucleophil.

Geranylgeranyl- and farnesyl pyrophosphate are endogenous metabolites found in all mammalian cells that undergo a wide range of transferase reactions that all have in common the fact that the pyrophosphate acts as a leaving group and the alkene forms a carbocation. The latter alkyates the other substrate in the enzyme reaction. For those agents not convertible to alkylating moieties, such as an alpha, beta unsaturated carbonyl, the effect would be a reversible inhibition. For the alkylating analogs, the potential exists for irreversible active-site directed alkylation. Thus, the invention includes any terpene which is 10 to 20 carbons in length and which either terminates in an alpha, beta unsaturated carbonyl or which is converted to such a metabolite in vivo.

For instance, there is a series of acyclic diterpenes closely related to geranylgeraniol that may be used in the invention. At present, only phytol and geranylgeraniol are commercially available. The others are isolated from their natural sources. Geranylgeraniol is naturally available as an isolate of linseed oil and cedrela toona wood. Phytol can be isolated from green plants. 9-hydroxygerarylgeraniol can be isolated from brown seaweed, geraryllinalool from jasmine oil and Norwegian spruce, and gerarylcitronellol from bumblebee secretion.

The pyrophosphate not only acts as a leaving group, but the free pyrophosphate anion released acts as an ion-pair for the terpene carbocation. Thus the terpenes of the invention further include attachment of any substituent to C1 of the terpene that endows the compound with alkyating activity. Also included are terpenes having any leaving group other than pyrophosphate. However, this last group may be too unstable for use as a drug in humans and might cross cell membranes poorly because of its charge. These other leaving groups may have a structure that might interfere with the normal function of the free pyrophosphate anion. In general, preferable analogs are uncharged at physiologic pH, so as to promote uptake by tumor cells.

Geranylgeraniol, phytol and some diterpene analogs

Formula No:

12. Geranylgeraniol (Linseed Oil; Cedrela toona wood)

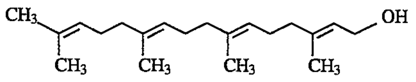

13. Phytol (All green plants)

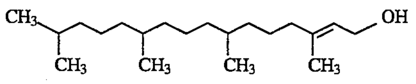

14. 9-Hydroxygeranylgeraniol (Brown seaweed)

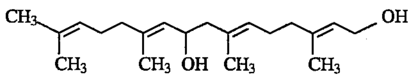

15. Geranyllinalool (Jasmine Oil; Norwegian spruce)

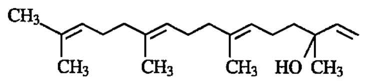

16. Geranylcitronellol (Bumblebee secretion)

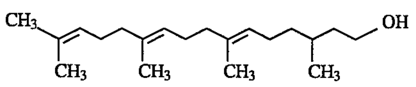

-continued

Sulfonic Acid Derivatives

Formula No.:

17. Methanesulfonate

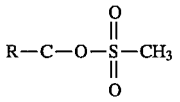

18. Sulfonamide

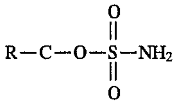

19. Ethanesulfonate

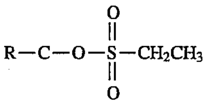

20. Sulfonylfluoride

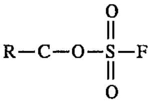

Phosphate analogs

Formula No.:

21. Methyl or ethyl phosphate

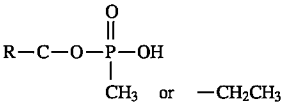

22. Methyl or ethyl, fluoro

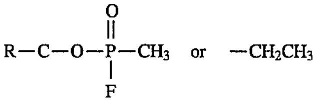

23. Phosphorothioate

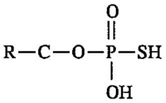

24. Dimethyl or methyl, ethyl or diethyl, phosphorothioate

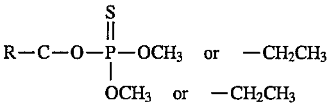

25. Dimethyl or ethyl, methyl or diethyl, phosphorodithioate

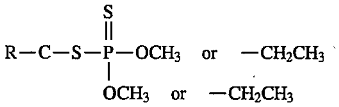

-continued

R Groups for derivatives and analogs numbers 17-25.

The Site of Attachment is at X.

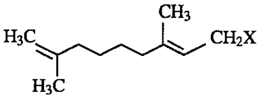

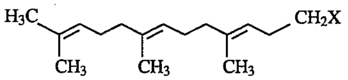

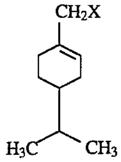

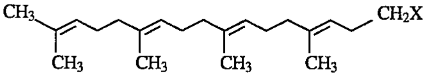

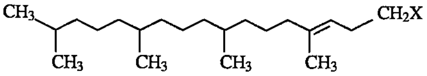

Cancer Therapy

Generally, prostate cancers and colon cancers are adenocarcinomas. However, in roughly five percent of the cases either of these cancers are some other type. An example of an astrocytoma is a glioblastoma. Examples of sarcomas include osteosarcomas, fibrosarcomas, and rhabdomyosarcomas. The cancer to be treated can be metastatic, locally expanding or locally invasive.

The administration of the terpene can be accomplished by any of a number of routes but it is usually either oral or topical with the oral route preferred. The oral route is preferred. The term "oral route" means that the patient would swallow the drug. The term also includes gavage, which is a preferred delivery in nonhuman animals.

Preferably the mammal treated is a human. For humans, the effective amount of terpene is selected from a range of from about 9 milligrams per kilogram of body weight of the mammal per day (mg/kg/day) to about 0.10 grams per kilogram of body of the mammal per day (gm/kg/day). A more preferred effective amount is selected from the range of about 0.02 to about 0.15 gm/kg/day. A single daily administration is typical, but the dose can be given two, three or more times a day. The terpene is usually administered on a long-term basis or chronically for weeks, months, or years.

The terpenes of the invention can be stored at room temperature, preferably protected from bright light and away from direct heat. The pleasant taste and odor of these terpenes permit their use undiluted, mixed with liquid or given with food. Juices, dairy products, and mashed fruits make particularly suitable vehicles for oral consumption. Alternatively, the terpene can be presented in encapsulated form, in a syrup, a gel, a lozenge or other conventional means for delivering oral medication. Additionally, the terpene can be diluted to a preselected concentration in a liquid such as a saccharide based syrup. The patient is given (or instructed to take) a specified volume, such as a tablespoonful, which can be taken alone or mixed in liquid or semi-liquid comestibles as noted above.

Sensitizing a Cancer to Radiation

The invention also includes a method of sensitizing a cancer to radiation comprising administering an effective amount of a chosen terpene to a mammal having the cancer. The terpene is selected from the group consisting of a cyclic monoterpene, a noncyclic monoterpene, a noncyclic sesquiterpene, and a noncyclic diterpene. The cancer is preferably either prostatic or colonic. The cancer may be selected from a group of adenocarcinoma, astrocytoma, and sarcoma. The adenocarcinoma is preferably either prostatic or colonic. The astrocytoma is preferably a glioblastoma. The sarcoma is preferably an osteosarcoma, a fibrosarcoma, or a rhabdomyosarcoma.

The administration is either oral or topical with the oral route preferred. Preferably the mammal is a human and the administration is once to three times a day. The cancer can be either locally expanding, locally invasive or metastatic. The effective amount for humans is selected from a range of from 9 mg/kg/day to about 0.10 gm/kg/day. More preferably, the effect of the amount is selected from a range of about 0.02 to about 0.15 gm/kg/day. The acyclic monoterpene is preferably either beta myrcene or citral. The cyclic monoterpene is preferably limonene. The sesquiterpene is preferably selected from a group consisting of farnesol, farnesal, farnesylic acid and nerolidol. The diterpene is preferably selected from a group consisting of phytol, phytal, phytylic acid, geranylgeraniol, geranylgeranial, and geranylgeranylic acid.

Inhibition of Cancer Cell Growth

The invention also includes a method of inhibiting the growth of cancer cells comprising applying an effective amount of a selected terpene to the cancer cells. The cancer cells are chosen from the group consisting of prostate cancer, colon cancer, osteosarcoma and glioblastoma. The terpene is selected from a group consisting of beta myrcene, citral, limonene, farnesol, farnesal, farnesylic acid and nerolidol, phytol, phytal, phytylic acid, geranylgeraniol, geranylgeranial, and geranylgeranylic acid.

The application of the terpene to the cells is either direct or indirect. The cells can be located in a mammal. When the cells are located in a mammal the application is usually indirect and preferably oral. Direct application can be made topically. The mammal is preferably a human and the application is preferably once to three times a day. The effective amount for humans is selected from a range from about 9 mg/kg/day to about 0.10 gm/kg/day. A more preferred effective range is from about 0.02 to about 0.15 gm/kg/day.

Definitions

The term "effective amount" means a dosage sufficient to produce a desired result. The desired result can be subjective or objective improvement in the recipient of the dosage, a decrease in tumor size, a decrease in the rate of growth of cancer cells, and/or an enhanced sensitivity of cancer cells to radiation.

The terms "treating cancer", "therapy" and the like mean generally any improvement in the mammal having the cancer wherein the improvement can be ascribed to treatment with the terpene. The improvement can be either subjective or objective. For example, if the mammal is human, the patient may note improved vigor or vitality or decreased pain as subjective symptoms of improvement or response to therapy. Alternatively, the clinician may notice decrease in tumor size or tumor burden based on physical exam, laboratory parameters, tumor markers or radiographic findings.

Some laboratory signs that the clinician may observe for response to therapy include normalization of tests such as white blood cell count, red blood cell count, platelet count, erythrocyte sedimentation rate, and various enzyme levels such as transaminases and hydrogenases. Additionally, the clinician may observe a decrease in a detectable tumor marker such as prostatic specific antigen (PSA) or chorio embryonic antigen (CEA). Alternatively, other tests can be used to evaluate objective improvement such as sonograms, nuclear magnetic resonance testing and positron emissions testing.

"Inhibiting the growth of cancer cells" can be evaluated by any accepted method of measuring whether growth of the cancer cells has been slowed or diminished. This includes direct observation and indirect evaluation such as subjective symptoms or objective signs as discussed above.

The term "sensitizing a cancer to radiation" means that as a result of treatment with the terpene, the cancer is more likely to respond to radiation exposure than it would have been without treatment with the terpene. The term "respond to radiation" means that the cancer is expected to either regress or slow its growth subsequent to radiation therapy.

In referring to specific terpenes the corresponding alcohol, aldehyde and carboxylic acid are included. Such derivatives are sometimes referred to as "terpenoids." Additionally, active metabolites of the terpenes are included. For instance, the terms "limonene, farnesol, phytol and geranylgeraniol" include the active metabolites as well as the administered parent compounds or pro-drugs.

Dosage Conversions

In living animals, metabolic rate decreases as body size increases. For drugs that undergo metabolism or act by altering a metabolic event, drug dosing must take this into consideration. Body surface area correlates better with metabolic rate than does body weight. For this reason, it is best to use body surface area to convert dosing in one species to that of another. See Freireich, et al., Cancer Chemotherapies 50(4)219–244 (1966). Freireich provided correlation factors using body surface area to convert mouse doses to that of other species. A rat would get about one-half of the mouse dose; a monkey which weighs about three kilograms would get about one-fourth of the mouse dose; a dog which weighs about 8 kilograms would get one-sixth of the mouse dose and a human would get about one-twelfth of the mouse dose. Thus, a 14 gram dose in a mouse correlates to slightly over one gram in a human and a 126 gram dose in a mouse correlates to about eleven grams in a human. The mouse dose of the invention is selected from a range of from about 100 mg/kg/day to about 2 gm/kg/day. A more preferred range for the mouse is from about 0.2 to about 1.8 mg/kg/day.

The following examples are illustrative. The invention is not limited by the specification and illustrations, but rather by the appended claims.

EXAMPLES

Example 1: In vitro antitumor activity of selected terpenes against the PC3 human prostate carcinoma.

A human prostate carcinoma cell line, PC3, was obtained from the American Tissue Culture Collection, Accession No. CRL 1435. The PC3 cells were cultured in RPMI 1640 medium enriched with 10% fetal calf serum (FCS). The medium and the FCS are both available from GIBCO BRL Life Technologies, Inc., 8400 Helgeman Lane, Gaithersburg, Md. 20877.

Terpenes were exposed to the PC3 cells as follows. On day 0, seed PC3 cells at about 1,000 cells per well were placed in each well of a 96-well tissue culture plate along with 0.1 millimeter (ml) of culture medium. On day 1, various concentrations of each of the selected terpenes were added. A serial dilution of each terpene was made in dimethyl sulfoxide (DMSO). All of the initial concentrations were about 200 times the desired concentration. Each dose was further diluted 100 times with culture medium. 0.1 ml of each dose was added per well to the tissue culture plate. The plates were incubated at 37° Celsius (C) under 5% carbon dioxide ($CO_2$) for seven days. The results are depicted graphically in FIGS. 1–9 and some of the concentrations which inhibited cell growth to about 50% of the control growth ($IC_{50}$) are shown in Table 1.

TABLE 1

In vitro antitumor activity of selected terpenes against the PC3 human prostate carcinoma (Seven day exposure)

| | Terpene | IC50 in μM | μg/ml |
|---|---|---|---|
| 1. | d-Limonene | 217 | 30 |
| 2. | beta-myrcene | 147 | 21 |
| 3. | citral | 17 | 3 |
| 4. | trans, trans-farnesol | 85.6 | 19 |
| 5. | farnesylic acid | 63.2 | 15 |
| 6. | nerolidol | 90.1 | 20 |
| 7. | phytol | 34.3 | 10 |
| 8. | geranylgeraniol | 10.5 | 3.0 |

FIGS. 1–6 show that citral, nerolidol, farnesylic acid, trans-trans-farnesol, phytol, and geranylgeraniol all demonstrated favorable activity against the human prostate cancer cells.

Figure 7:
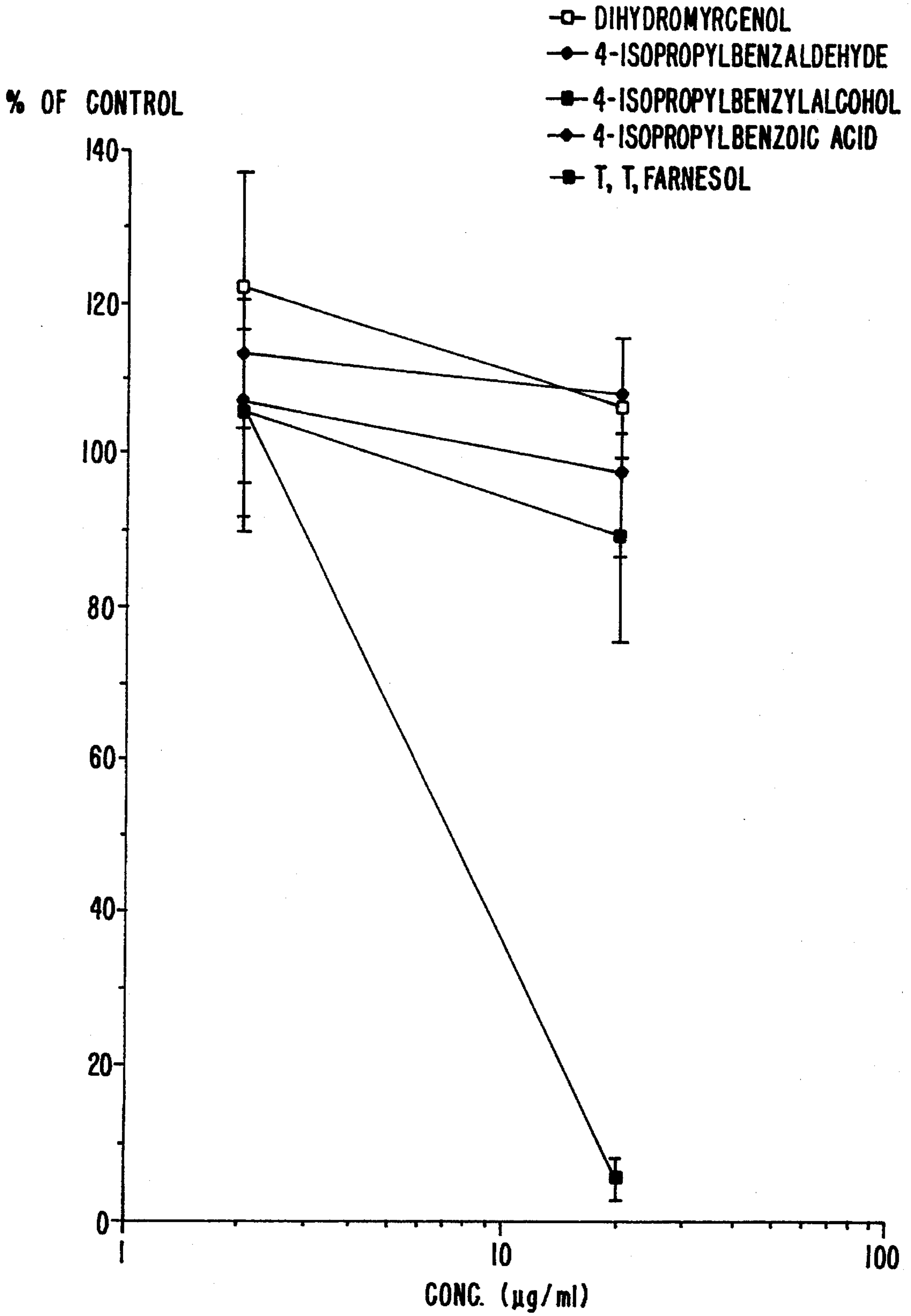
FIG. 7 displays the growth of human prostrate cancer cells as a percentage of untreated control cells when the cancer cells were treated with each of the four named terpenes as compared to farnesol, which is also graphed, in terms of μg/ml.
Figure 8:
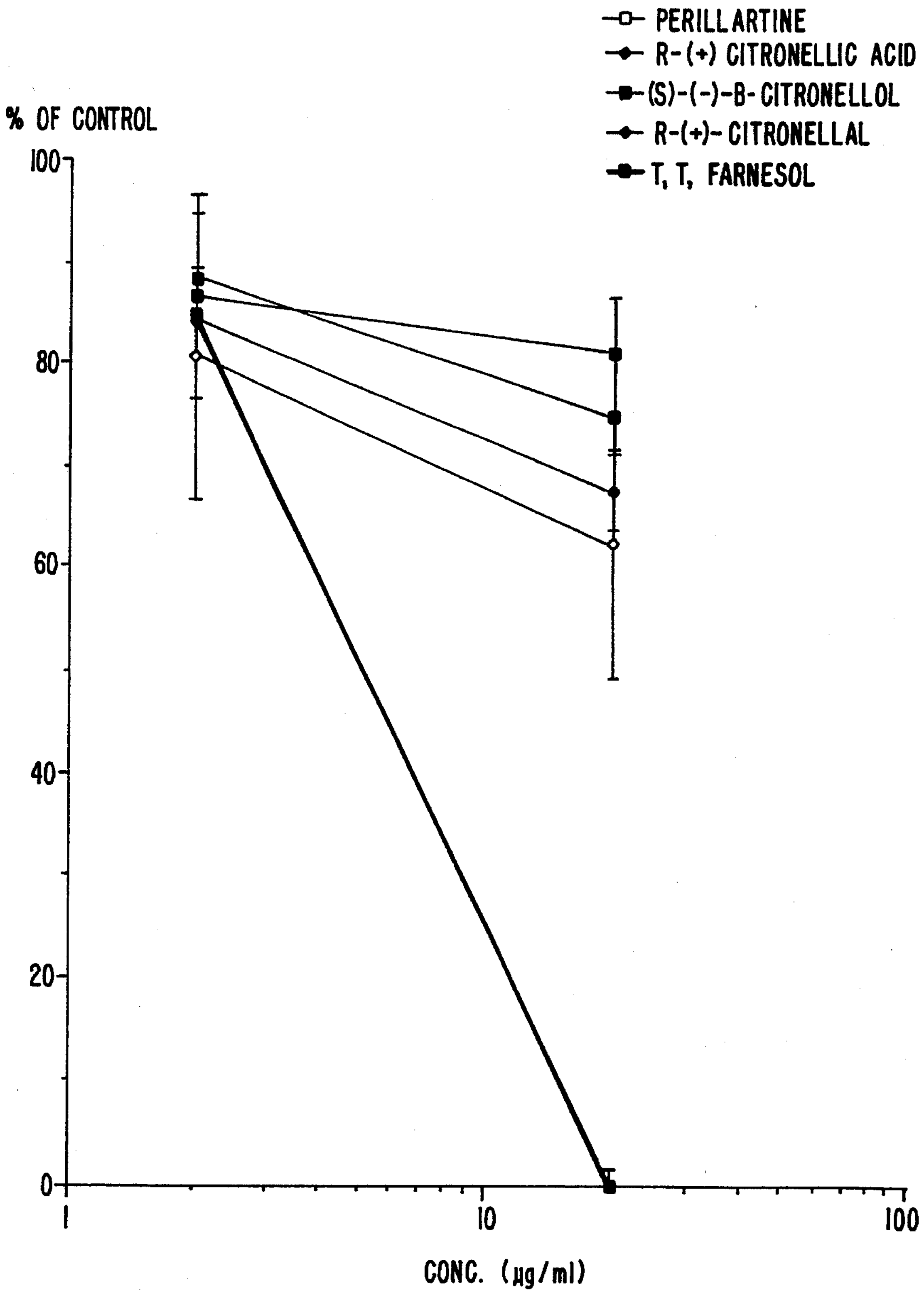
FIG. 8 displays the growth of human prostrate cancer cells as a percentage of untreated control cells when the cancer cells were treated with each of the additional four named terpenes as compared to farnesol, which is also graphed, in terms of μg/ml.
Figure 9:
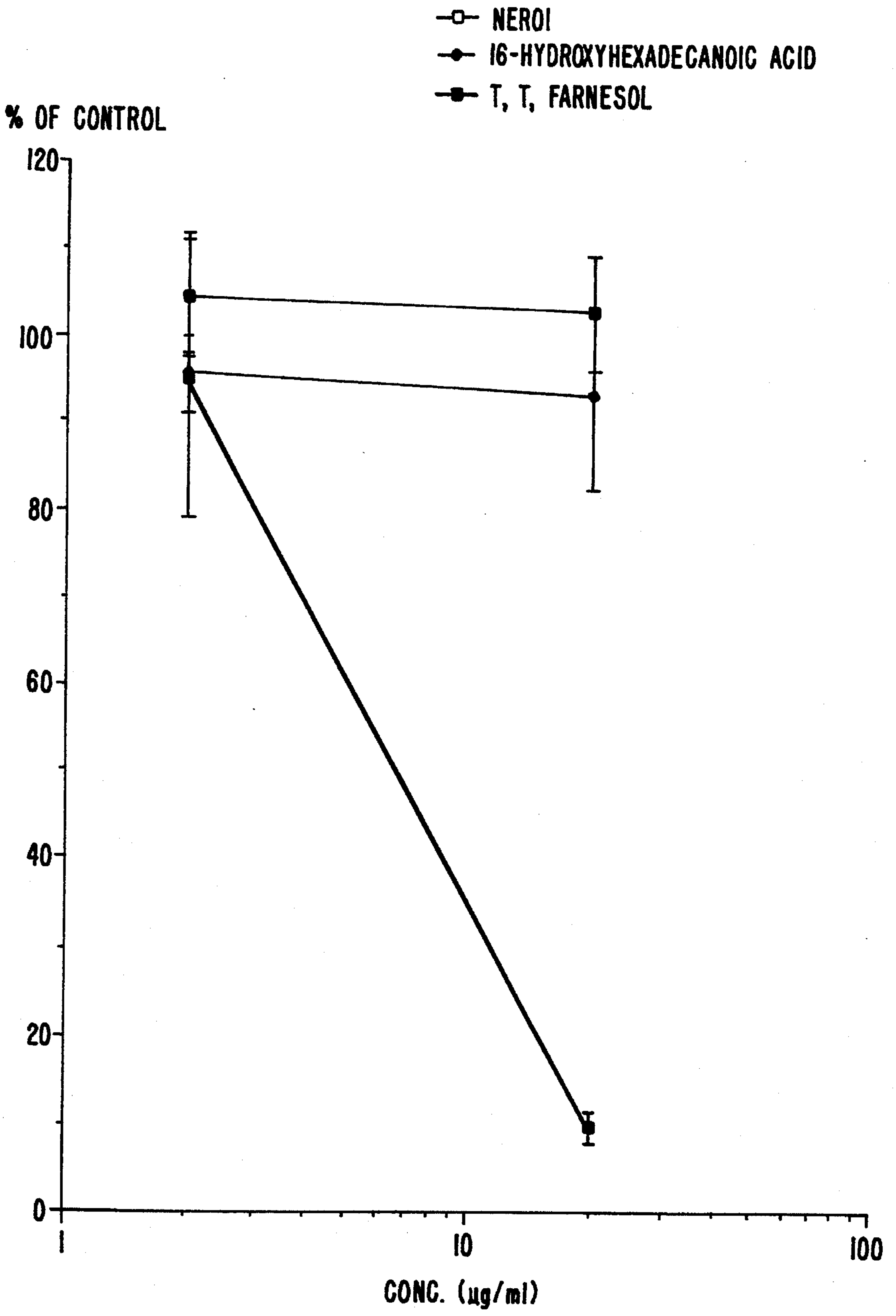
FIG. 9 displays the growth of human prostrate cancer cells as a percentage of untreated control cells when the cancer cells were treated with each of the additional two named terpenes as compared to farnesol, which is also graphed, in terms of μg/ml.

FIGS. 7–9 indicate that some additional terpenes were less active than farnesol, which was used as a standard in these figures. The less active compounds include dihydromyrcenol, 4-isopropylbenzaldehyde, 4-isopropylbenzylalcohol, 4-isopropylbenzoic acid, perillartine, citronellic acid, d-citronellol, citronellal, nerol and 16-hydroxyhexadecanoic acid.

Example 2: Effect of limonene on various tumor cell proliferations.

Limonene (Sigma) was evaluated for its effect on proliferation of various tumor cell lines. The cell lines included U87 and A172 (both are glioblastomas), HOS (a low ras osteosarcoma), AD5 (a high ras osteosarcoma), and HT29 (a high ras colon carcinoma). An activated or high ras means that the ras oncogene has mutated to a form which can transform normal cells to malignant cells. The glioblastoma cells were grown in RPMI 1640 culture medium and the other three cell lines were grown in Dulbecco's Modified Eagle's Medium (DMEM, available from GIBCO).

Limonene was added to the growth medium, which was supplemented with 10% FCS, and incubated at 37° C. for 24 hours. The medium was added to human tumor cells plated the previous day in 60 millimeter (mm) tissue culture (TC) dishes. After three to four days of continuous treatment, the cells were detached by trypsinization and counted using a hemocytometer (Hy-Lite Counting Chamber from Fisher Scientific, 711 Forbes Ave., Pittsburgh, Pa. 15219-4785). Cell viability was determined by a trypin blue exclusion method as described in detail in the manufacturer's instructions. As shown in Table 2, limonene provided a favorable $IC_{50}$ as measured in millimoles (mM).

TABLE 2

Effect of limonene on tumor cell proliferation

| Cell line | Growth Medium | Limonene IC50* (mM) |
|---|---|---|
| U87 glioblastoma | RPMI 1640 | 2.1 ± 0.4 |
| A172 glioblastoma | RPMI 1640 | 1.5 ± 0.5 |
| HOS osteosarcoma (low ras) | DMEM | 3.0 ± 0.3 |
| AD5 osteosarcoma (high ras) | DMEM | 4.8 ± 0.6 |
| HT29 colon carcinoma (high ras) | DMEM | 4.5 ± 0.5 |

*cell viability >95%, meaning that of the approximately 50% of cells which survived, >95% were viable.

Example 3: The effect of limonene on radiation sensitivity of tumor cells.

Radiation dosing in humans can be as low as 100 to 200 rads for a total body radiation therapy. The word "rad" refers to an absorbed radiation dose equal to 0.01 Joules (J)/kg of the absorbing medium such as tissue. For local radiation therapy isolating a tumor deposit, dosage can range from about 2,000 to 4,000 rads for lymphomas and up to about 6,000 to 7,000 rads for tumors such as prostate cancer that are normally radiation resistant.

Figure 10:
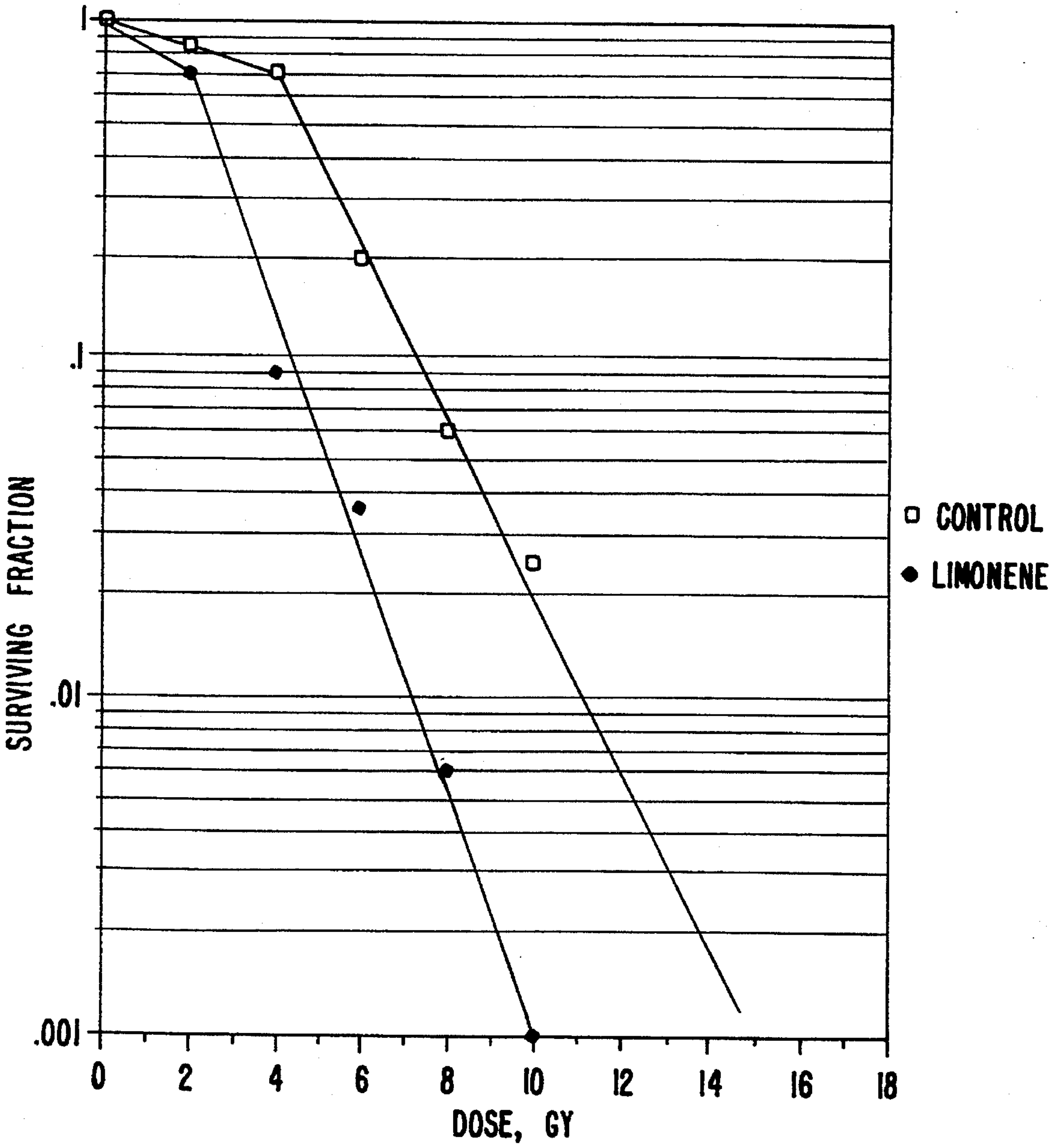
FIG. 10 is a radiation dose response curve plotting the surviving fraction of a human osteosarcoma cell line which is radioresistant via activated ras oncogene versus the dosage of radiation in gray (Gy), a metric unit for absorbed radiation dose.

An activated ras oncogene makes tumor cells resistant to radiation therapy. The AD5 human osteosarcoma cell line is an example of such a cell line resistant to radiation by virtue of an activated ras oncogene. AD5 cells were cultivated as described in Example 2. Limonene was prepared in various concentrations also as described in Example 2. FIG. 10 shows the radiation dose response of this cell line in the presence (diamonds) and in the absence (open boxes) of 3 mM limonene. Limonene alters both the shoulder and the dose (Do) of the radiation dose response curve. This dose refers to the dose that reduces the number of surviving cells to about 37% of the control cells. Gy (gray) is an international metric unit for an absorbed dose of radiation. One Gy equals one Joule/kg.

Example 4: Apoptosis and nuclear fragmentation.

Drugs can be cytostatic in that they suppress tumor growth, but do not kill. Other drugs kill tumor cells through either necrosis or apoptosis. The latter is also called programmed cell death and is a physiologic means of cell death. For example, lymphocytes exposed to glucocorticoids die by apoptosis. Involution of hormone sensitive tissue such as breast and prostate that occurs when the trophic hormone is removed occurs via apoptosis.

The invention examined the effect on prostate tumor cells of treatment with limonene, farnesol and phytol. With each of these compounds, tumor cell death (not cytostasis) was observed. Also, in each case, the mode of cell death was apoptosis, not necrosis. The classic signature of apoptosis is the cleavage of nuclear DNA into nucleosomal subunits. On gels, this gives rise to the appearance of a ladder as nucleosomal units are sequentially cleaved from the DNA. With each of these drugs, a classic DNA ladder indicative of apoptosis has been noted.

Figure 11:
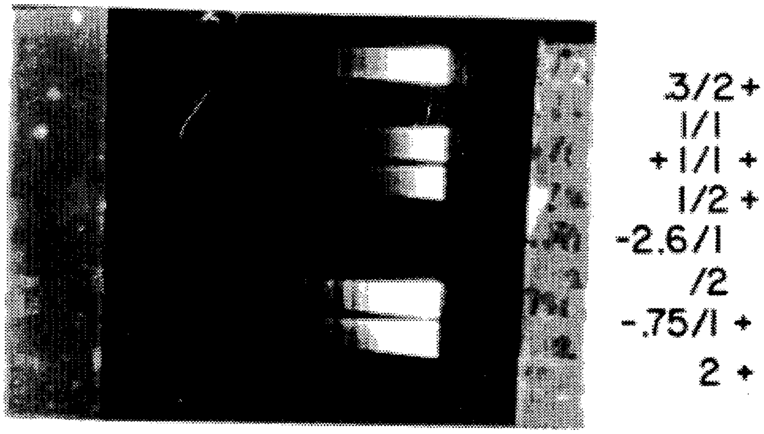
FIG. 11 is a gel photograph showing DNA ladders.

After drug exposure, cells were lysed and the high molecular DNA removed by centrifugation. The aqueous phase was treated with proteinase K to digest proteins. After a phenol/chloroform extraction, the DNA was precipitated with salt and ethanol. The pellet was dissolved in deionized water and treated with 500 μg/ml RNase A. The DNA was run on a 2% agarose minigel. FIG. 11 is a gel photograph showing classic DNA ladders for farnesol (F) and limonene (L). Cell death was verified by the demonstration of DNA fragmentation as represented by the ladder configurations on the gel.

Example 5: In vivo antitumor activity of d-limonene against PC3 human prostate carcinoma in nude mice.

Nude mice were obtained from Cancer Research Facility in Frederick, Md. The strain name is Athymic MCR-nude. PC3 cells were transplanted into both the right and left flanks of nude mice and allowed to grow until the tumor size reached the volume of approximately 200–300 cubic mm ($mm^3$). At this time, five mice bearing ten tumors total were allocated to each group.

The drug or vehicle alone were administered by gavage once daily Monday through Friday for two weeks. The control group received olive oil at a dose of 0.1 cubic centimeters (cc) per ten grams (gm) of body weight. Other groups received the same volume of olive oil with limonene added to give a daily dose of limonene of 0.1, 1.0 or 2.0 milligrams of drug per kilogram of body weight (mg/kg). Both body weight and tumor volume were measured daily.

Figure 12:
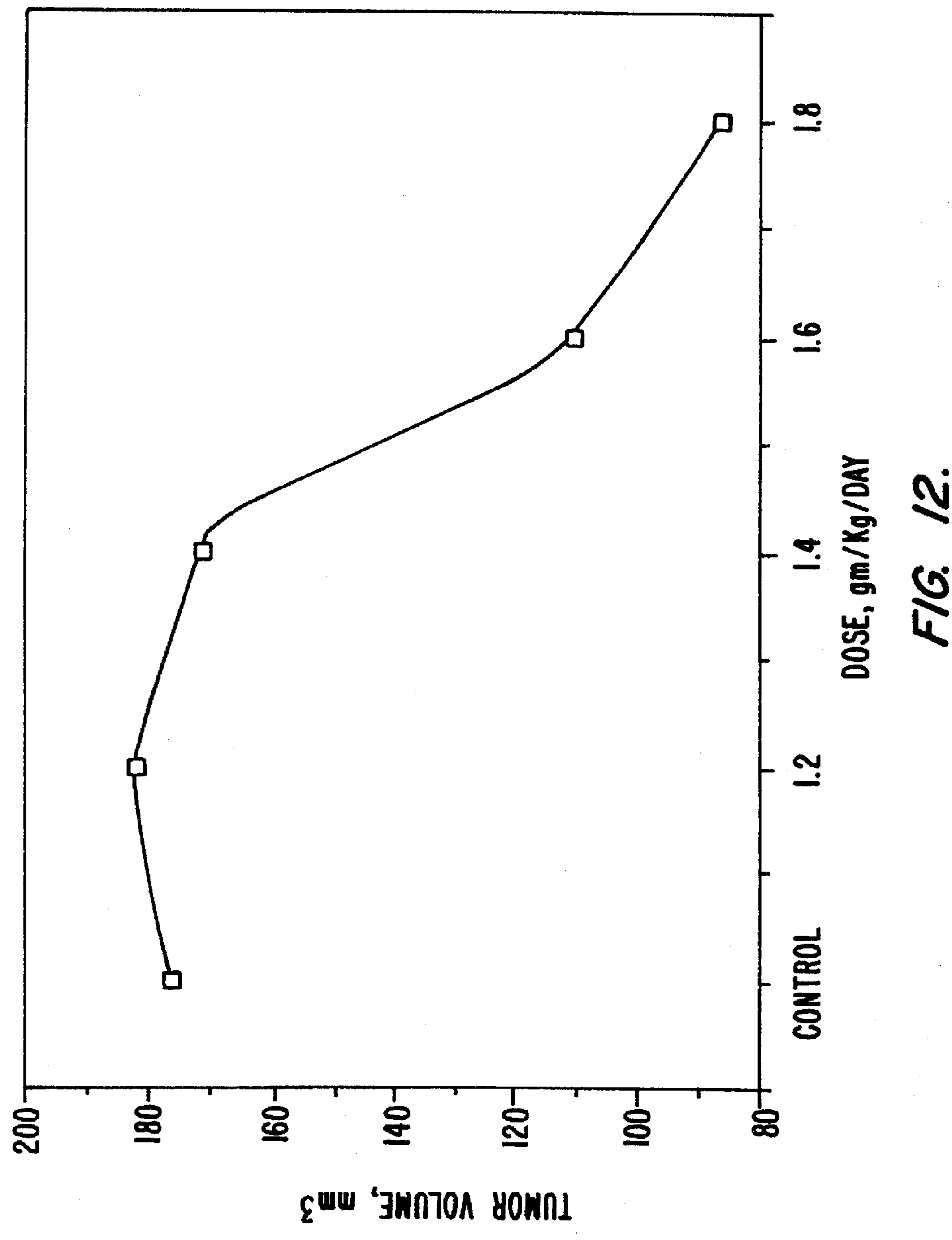
FIG. 12 displays data from an in vivo experiment as a dose response curve for phytol treatment of nude mice which were inoculated with human prostate cancer cells. The tumor volume, in cubic millimeters ($mm^3$), is plotted against the terpene dose in grams per kilogram of body weight per day (gm/kg/day).

The animals appeared to tolerate the drug well and even at the highest dose level there was not a statistically significant loss in weight over the course of the experiment. The rate of tumor growth was the same in the control group and those treated with 0.1 and 1.0 gm/kg. However, the rate of tumor growth in the animals receiving 2.0 gm/kg was approximately half of that in the control group. This result was highly significant with low p values for the differences in tumor volume (p=0.031) and rate of tumor growth (p=0.0022) by day 14 in the control as compared to the animals receiving limonene at 2 gm/kg. See FIG. 12 which plots the tumor volume in $mm^3$ against the dose of limonene in gm/kg/day.

Example 6: In vivo antitumor activity of phytol against PC3 human prostate carcinoma in nude mice.

Figure 13:
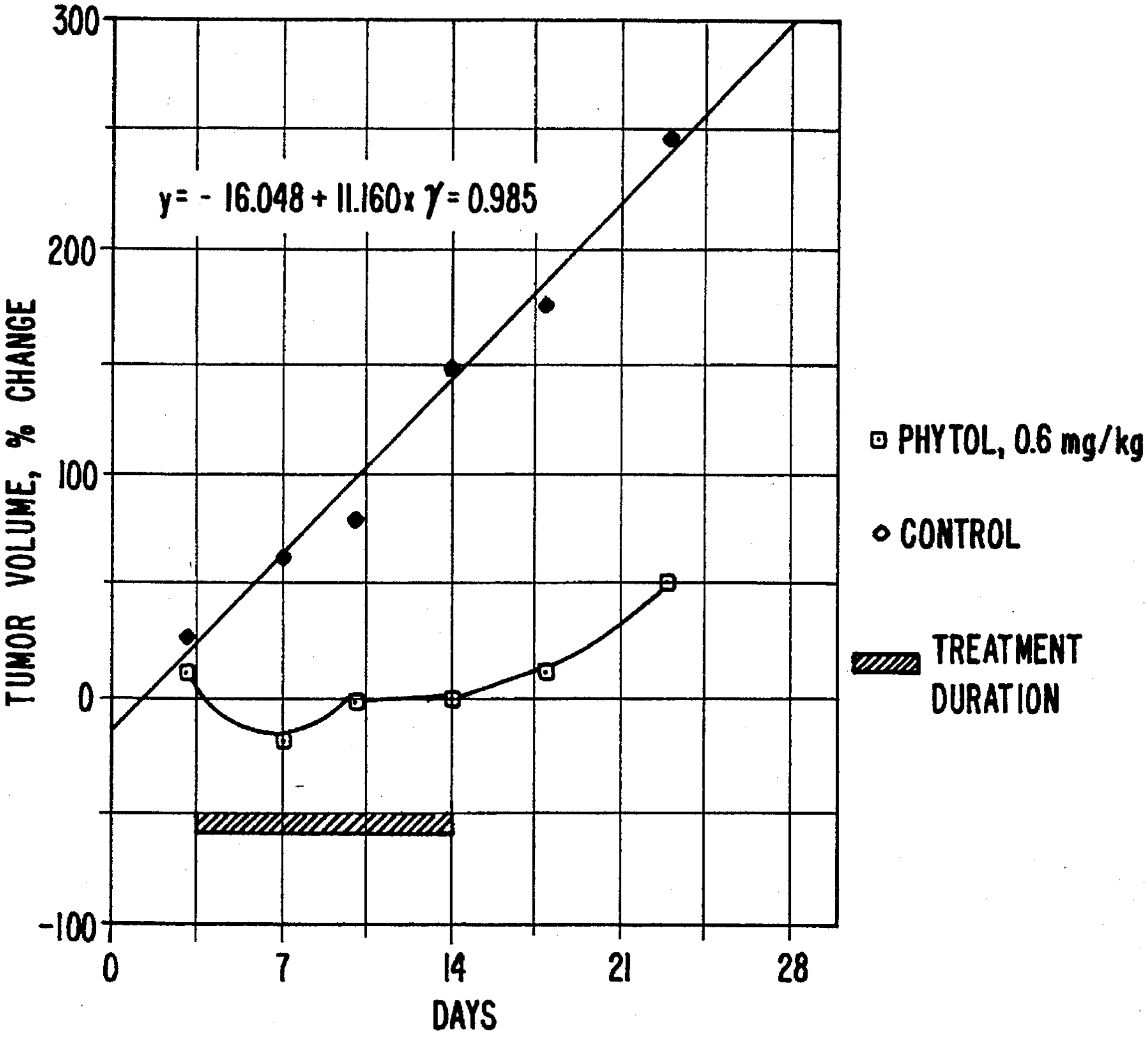
FIG. 13 displays data from an in vivo experiment as a dose response curve for limonene treatment of nude mice which were inoculated with human prostate cancer cells.

The experimental procedure of Example 5 was followed except that phytol was used in place of limonene. The animals tolerated the phytol well. The results are depicted in FIG. 13 which plots the percent change of tumor volume versus the number of days after inoculation of the nude mice with TC3 tumor cells. The treated animals (open squares) produced a lower tumor volume as compared to the control animals (closed diamonds). During the treatment period (indicated by a bar) the treated animals showed negligible tumor production.

The equation is obtained by applying a least squares regression of the equation y=b+mx to the data. The resulting equation is the best fit to the data. In this example, "y" represents the percentage change in tumor volume and "x" represents the number of days. The $\gamma$ value represents the "goodness" or satisfaction of the fit. If $\gamma$=1, then the fit is perfect. If $\gamma$=0, then there is no correlation. In this case, $\gamma$=0.985, demonstrating a nearly perfect fit.

Example 7: A clinical trial.

The patient selected for treatment is a man having prostate adenocarcinoma and who is not a candidate for surgical treatment. Because the patient weighs about 70 kilograms, the dosage selected can range from about 1 gram to about 11 grams total per day (about one-twelfth the mouse dose of 0.2 to 1.8 gm/kg/day) orally. This dose corresponds to about 2 ml to about 14 ml of undiluted drug. The patient is started on an intermediate dosage of 2 grams orally three times a day. The terpene is phytol.

The patient is monitored for symptoms and signs of drug toxicity such as loss of appetite. If toxicity is noted, the drug administration is suspended. Drug administration is reinstituted when the patient recovers but at a dosage reduced by about 25%. The phytol is administered on a long-term or chronic basis. Although the patient is monitored carefully throughout the entire treatment course, monitoring is most intensive during the first month of therapy.

Preferably, the response is arrest of tumor growth. Various means of assessing tumor growth are available including physical examination, determination of levels of prostate specific antigen, sonographic studies and radiographic evaluations. Additionally, parameters are monitored to assess the patient's general tolerance of the drug and well being. For example, blood or serum tests for complete blood counts, electrolytes, minerals, enzymes and various other factors may be monitored.

What is claimed is:

1. A method of treating prostate cancer comprising administering an effective amount of terpene to a mammal having prostate cancer, said terpene selected from the group consisting of a diterpene of the formula

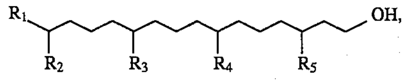

and a sesquiterpene of the formula

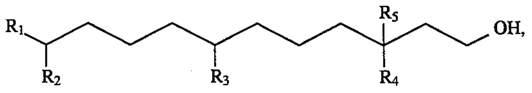

wherein $R_1$, $R_2$, $R_3$, $R_4$, and $R_5$ are selected from the group consisting of a hydrogen and a lower alkyl group, and wherein the terpene contains at least one site of unsaturation.

2. The method of claim 1 wherein the cancer is metastatic.

3. The method of claim 1 wherein the administration is either oral or topical.

4. The method of claim 1 wherein the mammal is a human.

5. The method of claim 4 wherein the effective amount is selected from a range of from about 9 mg/kg/day to about 0.10 gm/kg/day.

6. The method of claim 5 wherein the effective amount is selected from a range of from about 0.02 to about 1.15 mg/kg/day.

7. The method of claim 1 wherein the diterpene is either phytol or geranylgeraniol.

8. The method of claim 1 wherein the terpene is phytol.

9. A method of sensitizing prostate cancer to radiation comprising administering an effective amount of a terpene to a mammal having the cancer, said terpene selected from the group consisting of a diterpene of the formula

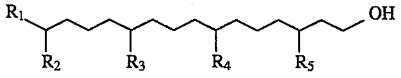

and a sesquiterpene of the formula

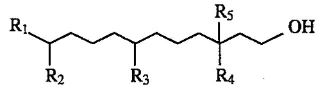

wherein $R_1$, $R_2$, $R_3$, $R_4$, and $R_5$ are selected from the group consisting of a hydrogen and a lower alkyl group, and wherein the terpene contains at least one site of unsaturation.

10. The method of claim 9 wherein the cancer is metastatic.

11. A method of inhibiting the growth of prostate cancer cells comprising applying an effective amount of a terpene to the cancer cells, said terpene selected from a group consisting of farnesol, phytol and geranylgeraniol.

12. The method of claim 11 wherein the application is indirect.

13. The method of claim 12 wherein the cancer cells are located in a mammal and the application is oral.

14. The method of claim 13 wherein the mammal is a human.

15. The method of claim 14 wherein the effective amount is selected from a range of from about 9 mg/kg/day to about 0.10 gm/kg/day.

16. The method of claim 15 wherein the effective amount is selected from a range of from about 0.02 to about 0.15 gm/kg/day.

17. The method of claim 13 wherein the application is made once a day.

18. A method of treating prostate cancer comprising administering an effective amount of geranylgeraniol to a mammal having the cancer.

19. A method of inhibiting the growth of prostate cancer cells comprising applying an effective amount of geranylgeraniol to the prostate cancer cells.

* * * * *